United States Patent [19]

Steinberg et al.

[11] Patent Number: 5,012,003
[45] Date of Patent: Apr. 30, 1991

[54] PROCESS FOR PREPARING DITHIOBISPHENOLS

[75] Inventors: David H. Steinberg, Bronx; John J. Luzzi, Carmel, both of N.Y.

[73] Assignee: Ciba-Geigy Corporation, Ardsley, N.Y.

[21] Appl. No.: 264,286

[22] Filed: Oct. 28, 1988

[51] Int. Cl.$^5$ .................................. C07C 148/02
[52] U.S. Cl. ................... 568/123; 568/744; 568/780; 568/781; 568/784
[58] Field of Search .............. 568/23, 744, 780, 781, 568/784

[56] References Cited

U.S. PATENT DOCUMENTS

| | | |
|---|---|---|
| 3,377,333 | 4/1968 | Ciesielski et al. ............ 568/23 |
| 3,377,334 | 4/1968 | McBride et al. ............. 568/23 |
| 3,423,389 | 1/1969 | Wheelus ................. 260/97.5 |
| 3,468,961 | 9/1969 | Geering et al. ............ 568/23 |
| 3,479,407 | 11/1969 | Laufer .................... 568/23 |
| 3,649,595 | 3/1972 | Kline ..................... 568/23 |
| 3,812,192 | 5/1974 | Gabler et al. ............. 568/23 |
| 3,919,171 | 11/1975 | Martin ................... 568/48 |
| 3,952,064 | 4/1976 | Whalley .................. 568/64 |

*Primary Examiner*—Mary E. Ceperley
*Attorney, Agent, or Firm*—Harry Falber

[57] ABSTRACT

An improved process for preparing dithiobisphenols comprising reacting an appropriate phenol with an alkali metal hydride, an alkaline earth metal hydride or mixtures thereof and subsequently reacting the product thereof with sulfur monochloride.

13 Claims, No Drawings

PROCESS FOR PREPARING DITHIOBISPHENOLS

Dithiobisphenols are known for a variety of uses. For example, U.S. Pat. No. 3,377,333, U.S. Pat. No. 3,377,334 and U.S. Pat. No. 3,423,389, among others, disclose the use of such materials as catalysts and bleaching agents in rosin acid esterification.

It is also known that the dithiobisphenols can be synthesized in a variety of manners. A dominant procedure is the reaction of phenols with sulfur monochloride in a variety of solvents. The above noted patents as well as U.S. Pat. No. 3,479,407, U.S. Pat. No. 3,649,595, and the like, describe such a process. However, such an approach generally results in over-sulfidation and a concomitant formation of undesirable polysulfides, thereby significantly lowering the yield of disulfide. Subsequent purification of these mixtures is difficult such that significant yield increase is not achieved.

Other approaches involving oxidation and reduction reactions are also known. However, the starting materials in these reactions are generally more expensive or require a multi-step synthesis. In addition, mono- and polysulfides have been prepared by the reaction of a phenol with either sulfur chloride (U.S. Pat. No. 3,812,912, U.S. Pat. No. 3,919,171, U.S. Pat. No. 3,952,064) or elemental sulfur (U.S. Pat. No. 3,468,961).

Accordingly, it is a primary object of the present invention to provide a process for synthesizing dithiophenols in high yields.

It has now been discovered that dithiophenols can be readily prepared by reacting phenols with an alkali metal hydride, an alkaline earth metal hydride or mixtures thereof to form a reactive alkylated sodium phenolate intermediate, which intermediate is reacted with sulfur monochloride. Advantages stemming from this approach include:

1. The process of the invention allows for the preparation of dithiobisphenols in high yield.
2. The process of the invention utilizes moderate temperatures avoiding the problems and cost associated with higher temperature processes.
3. The process of the invention allows for selective preparation of dithiobisphenols without substantial over sulfidation resulting in polynuclear by-products or polysulfides.
4. The process avoids the use of dipolar aprotic solvents used heretofore in various synthetic approaches directed to the synthesis of dithiophenols.
5. The process is particularly applicable for the preparation of 2,2'-dithiobis(4,6-di-tert.butyl-phenol) which is a preferred element in rosin acid esterification procedures.

The process of the invention involves reacting a phenol of the formula

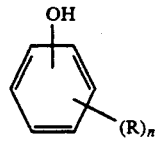

wherein each R is independently selected from the group consisting of $C_1$–$C_{18}$ alkyl, $C_5$–$C_{12}$ cycloalkyl, $C_7$–$C_9$ aralkyl or $C_7$–$C_9$ aralkyl substituted by $C_1$–$C_{12}$ alkyl; and n is 1–3; with an alkali metal hydride, an alkaline earth metal hydride or mixtures thereof to form a reactive alkylated phenolate intermediate, which intermediate is further reacted with sulfur monochloride to prepare dithiophenols of the formula

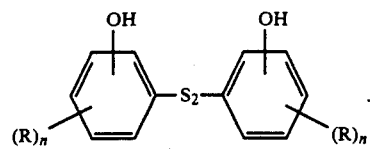

Preferred phenols exhibit R as $C_1$–$C_8$ alkyl, $C_5$–$C_6$ cycloalkyl, benzyl, alpha-methylbenzyl, and n as 2. Typical phenols include 2,4-di-tert.butylphenol; 2,6-di-tert butylphenol, 2-methyl-6-tert.butylphenol; 2,4-di-tert.octylphenol and 2,4-dimethylphenol.

Suitable hydrides include sodium hydride, lithium hydride, potassium hydride, calcium hydride, strontium hydride, barium hydride and mixtures thereof. Sodium hydride is preferred. The hydride is present in an amount ranging from about 0.7 to about 1.1, preferably about 0.8 mole to about 1.0 mole, relative to the phenol.

The sulfur monochloride is generally employed in an amount ranging from about 0.4 mole to about 0.6 mole, preferably from about 0.45 mole to about 0.55 mole, and most preferably about 0.5 mole, relative to the phenol.

The reaction may be conducted in a solvent, preferably a hydrocarbon solvent such as toluene, xylene, benzene, hexane, heptane, cyclohexane, naphtholite, and the like.

The reaction is conducted at temperatures ranging from about $-30°$ C. to the boiling point of the solvent and, preferably, from about $-15°$ C. to about $+5°$ C. Subsequent isolation of the dithiobisphenol provides high yields of the dithio product.

The following example further illustrates an embodiment of the invention.

EXAMPLE 1

Suspension of 10.53 g (250 mmol) of sodium hydride (57% dispersed in mineral oil) in 200 ml of heptane at $-5°$ C. to $0°$ C. is admixed dropwise with 51.6 g (250 mmol) 2,4-di-tert.butyl phenol dissolved in 200 cc heptane over a 1.25 hour period. When the addition is complete, the reaction is allowed to warm to $15°$ C. and then heated to $40°$ C. and held 1–2 minutes. The reaction is then allowed to cool slowly to $28°$ C. over a period of 0.5 hours and then cooled to about $-5°$ C. to $0°$ C., whereupon 10 cc (125 mmol) of sulfur monochloride in about 75 ml of heptane is admixed therewith dropwise over a 1.75 hour period. When the addition is complete, the reaction mixture is allowed to warm to room temperature (1.5 hours and stirred for an addition 0.5 hours. The reaction mixture is filtered and washed with heptane and allowed to stand overnight. The filtrate is divided into 2 aliquots and the solvent is then removed and the reaction product dried overnight in vacuo. The residue from one aliquot is recrystallized from methanol to give 24.5 g of the product. The residue from the other aliquot is recrystallized from acetonitrile to give 23.4 g of the product.

What is claimed is:

1. A process for preparing compounds of the formula

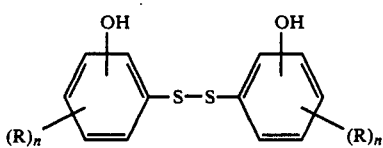

wherein each R is independently selected from the group consisting of $C_1$-$C_{18}$ alkyl, $C_5$-$C_{12}$ cycloalkyl, $C_7$-$C_9$ aralkyl or $C_7$-$C_9$ aralkyl substituted by $C_1$-$C_{12}$ alkyl, wherein the substituents on the respective phenol groups are the same and n is 1-3; which comprises reacting a phenol of the formula

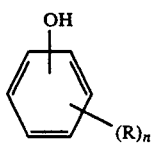

wherein R and n are as previously defined, with an alkali metal hydride, an alkaline earth metal hydride or mixtures thereof; and reacting the product thereof with sulfur monochloride.

2. The process of claim 1, wherein R is $C_1$-$C_8$ alkyl, $C_5$-$C_6$ cycloalkyl, benzyl, alpha-methyl benzyl and n is 2.

3. The process of claim 1, wherein said phenol is 2,4-di-tert.butylphenol, 2,6-di-tert.butyl-phenol, 2-methyl-6-tert.butylphenol or 2,4-di-tert-octylphenol.

4. The process of claim 1 wherein said alkali metal hydride is selected from the group consisting of sodium hydride, lithium hydride and potassium hydride.

5. The process of claim 4 wherein said alkali metal hydride is sodium hydride.

6. The process of claim 5 wherein said alkali metal hydride is present in an amount ranging from about 0.7 mole to about 1.1 mole relative to the phenol.

7. The process of claim 1 wherein a solvent is employed.

8. The process of claim 7 wherein said solvent is a hydrocarbon solvent.

9. The process of claim 8 wherein said hydrocarbon solvent is selected from the group consisting of toluene, xylene, benzene, hexane, heptane, cyclohexane, naphtholite.

10. The process of claim 9 wherein said hydrocarbon solvent is heptane.

11. The process of claim 6 wherein said alkali metal hydride is present in an amount ranging from about 0.8 mole to about 1.0 mole relative to the phenol.

12. The process of claim 1 wherein said sulfur monochloride is present in an amount ranging from about 0.4 mole to about 0.6 mole relative to the phenol.

13. The process of claim 1 wherein said sulfur monochloride is present in an amount ranging from about 0.45 mole to about 0.55 mole relative to the phenol.

* * * * *